United States Patent
Lowe et al.

(10) Patent No.: US 8,318,659 B2
(45) Date of Patent: *Nov. 27, 2012

(54) PEPTIDE-BASED ORGANIC SUNSCREENS

(75) Inventors: David J. Lowe, Wilmington, DE (US); John P. O'Brien, Oxford, PA (US); Antoinette E. Wilkins, Newark, DE (US)

(73) Assignee: E I du Pont de Nemours and Company, Wilmington, DE (US)

(*) Notice: Subject to any disclaimer, the term of this patent is extended or adjusted under 35 U.S.C. 154(b) by 1041 days.

This patent is subject to a terminal disclaimer.

(21) Appl. No.: 11/590,717

(22) Filed: Oct. 31, 2006

(65) Prior Publication Data

US 2007/0110686 A1    May 17, 2007

Related U.S. Application Data

(60) Provisional application No. 60/737,042, filed on Nov. 15, 2005.

(51) Int. Cl.
*A61K 38/00* (2006.01)
*A61K 38/04* (2006.01)
*A61K 8/00* (2006.01)
*A61K 8/18* (2006.01)
*A61K 8/64* (2006.01)
*A61K 8/65* (2006.01)
*C07K 5/00* (2006.01)
*C07K 7/00* (2006.01)
*C07K 16/00* (2006.01)
*C07K 17/00* (2006.01)
*A61Q 17/04* (2006.01)

(52) U.S. Cl. ......... 514/1.1; 530/326; 424/59; 424/70.14

(58) Field of Classification Search ............ None
See application file for complete search history.

(56) References Cited

U.S. PATENT DOCUMENTS

| | | | |
|---|---|---|---|
| 5,219,558 A | 6/1993 | Woodin, Jr. et al. | |
| 5,451,390 A | 9/1995 | Hartmann et al. | |
| 5,672,330 A | 9/1997 | Hartmann et al. | |
| 5,762,914 A | 6/1998 | Hartmann et al. | |
| 5,876,699 A * | 3/1999 | DiSomma et al. | 424/59 |
| 7,220,405 B2 * | 5/2007 | Huang et al. | 424/70.6 |
| 7,309,482 B2 * | 12/2007 | Buseman-Williams et al. | 424/59 |
| 7,736,633 B2 * | 6/2010 | Beck et al. | 424/70.6 |
| 7,964,180 B2 * | 6/2011 | Beck et al. | 424/70.14 |
| 2002/0098524 A1 | 7/2002 | Murray et al. | |
| 2003/0152976 A1 | 8/2003 | Janssen et al. | |
| 2005/0050656 A1 | 3/2005 | Huang et al. | |
| 2005/0226839 A1 | 10/2005 | Huang et al. | |
| 2005/0249682 A1 | 11/2005 | Buseman-Williams et al. | |
| 2006/0174423 A1 | 8/2006 | Rothe et al. | |

FOREIGN PATENT DOCUMENTS

| | | |
|---|---|---|
| EP | 1 273 308 A1 * | 1/2003 |
| WO | WO 90/02135 * | 3/1990 |
| WO | WO 01/79479 A2 | 10/2001 |
| WO | WO2004/000257 * | 12/2003 |
| WO | WO 2004/048399 A2 | 6/2004 |

OTHER PUBLICATIONS

Machine translation (English) for WO 2004/000257. Date Dec. 2003. 19 pages.*
Arai et al. Design of the linkers which effectively separate domains of a bifunctional fusion protein. Protein Eng. (2001) 14 (8): 529-532.*
Carter. Conjugation of Peptide to Carrier Proteins via m-Maleimidobenzoyl-N-Hydroxysuccinimide Ester (MBS) in The Protein Protocols Handbook, Humana Press Inc., Totowa, NJ 1996, pp. 689-692.*

* cited by examiner

*Primary Examiner* — Marcela M Cordero Garcia
(74) *Attorney, Agent, or Firm* — Roger W. Herrell, Jr.

(57) ABSTRACT

Peptide-based organic sunscreens, formed by coupling a skin-binding peptide with an organic sunscreen agent, are described. The skin-binding peptide part of the peptide-based organic sunscreen binds strongly to the skin, thus keeping the organic sunscreen agent attached to the skin for long lasting protection. Sunscreen compositions comprising the peptide-based organic sunscreens are also provided.

20 Claims, No Drawings

US 8,318,659 B2

PEPTIDE-BASED ORGANIC SUNSCREENS

CROSS-REFERENCE TO RELATED APPLICATION

This application claims priority under 35 U.S.C. §119 from U.S. Provisional Application Ser. No. 60/737,042, filed Nov. 15, 2005.

FIELD OF THE INVENTION

The invention relates to the field of personal care products. More specifically, the invention relates to peptide-based organic sunscreens formed by coupling a skin-binding peptide with an organic sunscreen agent.

BACKGROUND OF THE INVENTION

The harmful effects of ultraviolet radiation from sunlight are well documented. The major short-term hazard of exposure to ultraviolet radiation is sunburn, which is caused primarily by ultraviolet radiation of wavelengths between 290 to 320 nanometers (UVB radiation). Ultraviolet radiation in the wavelength range of 320 to 400 nanometers (UVA radiation) also contributes to sunburn. Long term hazards of ultraviolet radiation exposure include malignant changes in the skin surface leading to skin cancer and premature aging of the skin.

Sunscreens are well known and frequently used personal care products designed to protect the skin from the harmful effects of ultraviolet radiation from the sun. These sunscreen products contain sunscreen agents which absorb or scatter harmful ultraviolet radiation. The problem with current sunscreen products is that they are easily rubbed off or washed off by perspiration or swimming. Consequently, frequent reapplication is required to maintain protection. To address the lack of durability of sunscreen products, polymers, heavy waxes and oils are added to the compositions to impart water resistance (for example, Woodin et al., U.S. Pat. No. 5,219, 558). However, the use of these additives has not been entirely successful. A long-lasting, durable sunscreen with improved water resistance would represent an advance in the art.

In order to improve the durability of hair and skin care products, peptide-based hair conditioners, hair colorants, and other benefit agents have been developed (Huang et al., copending and commonly owned U.S. Patent Application Publication No.2005/0050656, and U.S. Patent Application Publication No. 2005/0226839). The peptide-based conditioners or colorants are prepared by coupling a specific peptide sequence that has a high binding affinity to hair or skin with a conditioning or coloring agent, respectively. The peptide portion binds to the hair or skin, thereby strongly attaching the conditioning or coloring agent. Additionally, peptide-based inorganic sunscreens comprising a skin-binding peptide coupled to an inorganic metal oxide sunscreen agent are described by Buseman-Williams et al. (copending and commonly owned U.S. Patent Application Publication No. 2005/0249682). However, sunscreens formed by coupling a skin-binding peptide to an organic sunscreen agent have not been described.

Peptides having a binding affinity to hair and skin have been identified using phage display screening techniques (Huang et al., supra; Estell et al. WO 0179479; Murray et al., U.S. Patent Application Publication No. 2002/0098524; Janssen et al., U.S. Patent Application Publication No. 2003/0152976; and Janssen et al., WO 04048399). Additionally, empirically generated hair and skin-binding peptides that are based on positively charged amino acids have been reported (Rothe et., WO 2004/000257).

In view of the above, a need exists for organic sunscreens that provide improved durability for long lasting effects and are easy and inexpensive to prepare.

Applicants have addressed the stated need by designing peptide-based organic sunscreens formed by coupling skin-binding peptides, which bind to skin with high affinity, to organic sunscreen agents to give sunscreens that provide long lasting protection.

SUMMARY OF THE INVENTION

The invention provides peptide-based organic sunscreens formed by coupling a skin-binding peptide with an organic sunscreen agent. Accordingly, in one embodiment the invention provides a peptide-based organic sunscreen having the general structure:

$(SBP_m)_n$-$(OSCA)_y$, wherein
a) SBP is a skin-binding peptide;
b) OSCA is an organic sunscreen agent;
c) m ranges from 1 to about 100;
d) n ranges from 1 to about 100; and
e) y ranges from 1 to about 100.

In another embodiment, the invention provides a peptide-based organic sunscreen having the general structure:
$[(SBP)_x$-$S_m]_n$-$(OSCA)_y$, wherein
a) SBP is a skin-binding peptide;
b) OSCA is an organic sunscreen agent;
c) S is a spacer;
d) x ranges from 1 to about 10;
e) m ranges from 1 to about 100;
f) n ranges from 1 to about 100; and
g) y ranges from 1 to about 100.

In another embodiment, the invention provides a sunscreen composition comprising an effective amount of a peptide-based organic sunscreen.

The invention also provides methods for forming a protective layer of a peptide-based organic sunscreen on the skin or lips comprising applying the sunscreen composition of the invention to the skin or lips and allowing the formation of the protective layer.

In another embodiment, the invention provides a method for forming a protective layer on skin or lips comprising the steps of:
a) providing a sunscreen composition comprising a peptide-based organic sunscreen selected from the group consisting of:
  i) $(SBP_m)_n$-$(OSCA)_y$; and
  ii) $[(SBP)_x$-$S_m]_n$-$(OSCA)_y$
  wherein
  1) SBP is a skin-binding peptide;
  2) OSCA is an organic sunscreen agent;
  3) n ranges from 1 to about 100;
  4) S is a spacer;
  5) m ranges from 1 to about 100;
  6) x ranges from 1 to about 10; and
  7) y ranges from 1 to about 100;
  and wherein the skin binding peptide is selected by a method comprising the steps of:
  A) providing a combinatorial library DNA associated peptides;
  B) contacting the library of (A) with a skin sample to form a reaction solution comprising DNA associated peptide-skin complexes;
  C) isolating the DNA associated peptide-skin complexes of (B);

D) amplifying the DNA encoding the peptide portion of the DNA associated peptide-skin complexes of (C); and
E) sequencing the amplified DNA of (d) encoding a skin-binding peptide, wherein the skin-binding peptide is identified; and b) applying the sunscreen composition of (a) to skin or lips and allowing the formation of said protective layer.

SEQUENCE DESCRIPTIONS

The invention can be more fully understood from the following detailed description and the accompanying sequence descriptions, which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

A Sequence Listing is provided herewith on Compact Disk. The contents of the Compact Disk containing the Sequence Listing are hereby incorporated by reference in compliance with 37 CFR 1.52(e). The Compact Disks are submitted in triplicate and are identical to one another. The disks are labeled "Copy 1—Sequence Listing", "Copy 2—Sequence Listing", and CRF. The disks contain the following file: CL3202 Seq Listing.ST25 having the following size: 8,000 bytes and which was created Oct. 30, 2006.

SEQ ID NOs:1-12, 17-33 are the amino acid sequences of skin-binding peptides.

SEQ ID NO:13 is the amino acid sequence of the protease Caspase 3 cleavage site.

SEQ ID NOs:14-16 are the amino acid sequences of peptide spacers.

DETAILED DESCRIPTION OF THE INVENTION

The present invention provides long lasting organic sunscreens formed by coupling a skin-binding peptide to an organic sunscreen agent. The peptide-based organic sunscreens may be used in sunscreen products and as an additive in skin care and cosmetic products to protect the skin from damage caused by ultraviolet radiation from the sun. The sunscreen compositions of the invention provide improved water resistance due to the affinity of the skin-binding peptide to the skin, thereby eliminating or reducing the need for reapplication of the composition after exposure of the skin to water. Additionally, the sunscreen compositions of the invention may be provided as a light spray-on formulation, free of the heavy waxes and oils commonly used to impart water resistance.

The following definitions are used herein and should be referred to for interpretation of the claims and the specification.

The term "invention" or "present invention" as used herein is a non-limiting term and is not intended to refer to any single embodiment of the particular invention but encompasses all possible embodiments as described in the specification and the claims.

"SBP" means skin-binding peptide.
"OSCA" means organic sunscreen agent.
"S" means spacer.

The term "peptide" refers to two or more amino acids joined to each other by peptide bonds or modified peptide bonds.

The term "skin-binding peptide" refers to peptide sequences that bind with high affinity to skin. The skin-binding peptides of the invention are from about 7 amino acids to about 50 amino acids, more preferably, from about 7 amino acids to about 25 amino acids, most preferably from about 7 to about 20 amino acids in length.

The term "DNA associated peptide" refers to a peptide having associated with it an identifying nucleic acid component. Typically, the DNA associated peptide is produced as a result of a display system such as phage display. In this system, peptides are displayed on the surface of the phage while the DNA encoding the peptides is contained within the attached glycoprotein coat of the phage. The association of the coding DNA within the phage may be used to facilitate the amplification of the coding region for the identification of the peptide.

The term "DNA associated peptide-skin complex" refers to a complex between skin and a DNA associated peptide wherein the peptide is bound to the skin via a binding site on the peptide.

The term "skin" as used herein refers to human skin, or substitutes for human skin, such as pig skin, Vitro-Skin® and EpiDerm™.

The terms "coupling" and "coupled" as used herein refer to any chemical association and includes both covalent and non-covalent interactions.

The term "stringency" as it is applied to the selection of the skin-binding peptides of the present invention, refers to the concentration of the eluting agent used to elute peptides from the skin. Higher concentrations of the eluting agent provide more stringent conditions.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "expression", as used herein, refers to the transcription and stable accumulation of sense (MRNA) or anti-sense RNA derived from the nucleic acid fragment of the invention. Expression may also refer to translation of mRNA into a polypeptide.

The term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The term "host cell" refers to a cell which has been transformed or transfected, or is capable of transformation or transfection by an exogenous polynucleotide sequence.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "phage" or "bacteriophage" refers to a virus that infects bacteria. Altered forms may be used for the purpose of the present invention. The preferred bacteriophage is derived from the "wild" phage, called M13. The M13 system can grow inside a bacterium, so that it does not destroy the cell it infects but causes it to make new phages continuously. It is a single-stranded DNA phage.

The term "phage display" refers to the display of functional foreign peptides or small proteins on the surface of bacteriophage or phagemid particles. Genetically engineered phage may be used to present peptides as segments of their native surface proteins. Peptide libraries may be produced by populations of phage with different gene sequences.

"PCR" or "polymerase chain reaction" is a technique used for the amplification of specific DNA segments (U.S. Pat. Nos. 4,683,195 and 4,800,159).

Standard recombinant DNA and molecular cloning techniques used herein are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., Experiments with Gene Fusions, Cold Spring Harbor Laboratory Press, Cold Spring Harbor, N.Y. (1984); and by Ausubel, F. M. et al., *Current Protocols in Molecular Biology*, published by Greene Publishing Assoc. and Wiley-Interscience (1987).

The invention provides peptide-based organic sunscreens formed by coupling a skin-binding peptide to an organic sunscreen agent. The skin-binding peptide may be identified using combinatorial methods, such as phage display. Alternatively, the skin-binding peptide may be generated empirically. The skin-binding peptide is coupled to an organic sunscreen agent, either directly or via an optional spacer, using covalent or non-covalent attachment. The peptide-based organic sunscreens may be used in sunscreen products and as an additive in skin care and cosmetic products to protect the skin from damage caused by ultraviolet radiation from the sun.

Skin-Binding Peptides

Skin-binding peptides (SBP), as defined herein, are peptide sequences that bind with high affinity to skin. The skin-binding peptides of the invention are from about 7 amino acids to about 50 amino acids, more preferably, from about 7 amino acids to about 25 amino acids, most preferably from about 7 to about 20 amino acids in length. Suitable skin-binding peptides may be selected using methods that are well known in the art or may be generated empirically.

The skin-binding peptides may be generated randomly and then selected against a specific skin sample based upon their binding affinity for skin, as described by Huang et al. in copending and commonly owned U.S. Patent Application Publication No. 2005/0050656, which is incorporated herein by reference. The generation of random libraries of peptides is well known and may be accomplished by a variety of techniques including, bacterial display (Kemp, D. J.; Proc. Natl. Acad. Sci. USA 78(7):4520-4524 (1981), and Helfman et al., Proc. Natl. Acad. Sci. USA 80(1):31-35, (1983)), yeast display (Chien et al., Proc Natl Acad Sci USA 88(21):9578-82 (1991)), combinatorial solid phase peptide synthesis (U.S. Pat. Nos. 5,449,754, 5,480,971, 5,585,275, 5,639,603), and phage display technology (U.S. Pat. Nos. 5,223,409, 5,403,484, 5,571,698, 5,837,500). Techniques to generate such biological peptide libraries are well known in the art. Exemplary methods are described in Dani, M., *J. of Receptor & Signal Transduction Res.*, 21(4):447-468 (2001), Sidhu et al., *Methods in Enzymology* 328:333-363 (2000), and *Phage Display of Peptides and Proteins, A Laboratory Manual*, Brian K. Kay, Jill Winter, and John McCafferty, eds.; Academic Press, NY, 1996. Additionally, phage display libraries are available commercially from companies such as New England Biolabs (Beverly, Mass.).

A preferred method to randomly generate peptides is by phage display. Phage display is an in vitro selection technique in which a peptide or protein is genetically fused to a coat protein of a bacteriophage, resulting in display of fused peptide on the exterior of the phage virion, while the DNA encoding the fusion resides within the virion. This physical linkage between the displayed peptide and the DNA encoding it allows screening of vast numbers of variants of peptides, each linked to a corresponding DNA sequence, by a simple in vitro selection procedure called "biopanning". In its simplest form, biopanning is carried out by incubating the pool of phage-displayed variants with a target of interest, washing away unbound phage, and eluting specifically bound phage by disrupting the binding interactions between the phage and the target. The eluted phage is then amplified in vivo and the process is repeated, resulting in a stepwise enrichment of the phage pool in favor of the tightest binding sequences. After 3 or more rounds of selection/amplification, individual clones are characterized by DNA sequencing.

The skin-binding peptides may be identified using the following process. After a suitable library of DNA associated peptides has been generated using phage display, bacterial display, or yeast display, as described above, the library is contacted with an appropriate amount of skin sample to form a reaction solution. Human skin samples may be obtained from cadavers or in vitro human skin cultures. Additionally, pig skin, Vitro-Skin® (available from IMS inc., Milford, Conn.) and Epiderm™ (available from Mattek corp., Ashland, Mass.) may be used as substitutes for human skin. The library of DNA associated peptides is dissolved in a suitable solution for contacting the skin sample. In one embodiment, the library of DNA associated peptides is dissolved in a buffered aqueous saline solution containing a surfactant. A suitable solution is Tris-buffered saline (TBS) with 0.5% Tween® 20. The solution may be agitated by any means in order to increase the mass transfer rate of the DNA associated peptides to the skin surface, thereby shortening the time required to attain maximum binding. The time required to attain maximum binding varies depending on a number of factors, such as size of the skin sample, the concentration of the peptide library, and the agitation rate. The time required can be determined readily, by one skilled in the art, using routine experimentation. Typically, the contact time is 10 minutes to one hour. Optionally, the library of DNA associated peptides may be contacted with a non-target, such as hair or plastic, either prior to or simultaneously with contacting the skin sample to remove the undesired DNA associated peptides that bind to the non-target.

Upon contact, a number of the randomly generated DNA associated peptides will bind to the skin to form a DNA associated peptide-skin complex. Unbound peptide may be removed by washing. After all unbound material is removed, DNA associated peptides having varying degrees of binding affinities for skin may be fractionated by selected washings in buffers having varying stringencies. Increasing the stringency of the buffer used increases the required strength of the bond between the peptide and skin in the DNA associated peptide-skin complex.

A number of substances may be used to vary the stringency of the buffer solution in peptide selection including, but not limited to, acidic pH (1.5-3.0); basic pH (10-12.5); high salt concentrations such as $MgCl_2$ (3-5 M) and LiCl (5-10 M); water; ethylene glycol (25-50%); dioxane (5-20%); thiocyanate (1-5 M); guanidine (2-5 M); urea (2-8 M); and various concentrations of different surfactants such as SDS (sodium dodecyl sulfate), DOC (sodium deoxycholate), Nonidet P40, Triton X-100, Tween® 20, wherein Tween® 20 is more typical. These substances may be prepared in buffer solutions including, but not limited to, Tris-HCl, Tris-buffered saline, Tris-borate, Tris-acetic acid, triethylamine, phosphate buffer, and glycine-HCl, wherein Tris-buffered saline solution is preferred.

It will be appreciated that DNA associated peptides having increasing binding affinities for skin may be eluted by repeating the selection process using buffers with increasing stringencies.

The DNA associated peptide-skin complexes may then be contacted with an eluting agent for a period of time, typically, 1 to 30 minutes, to dissociate the DNA associated peptides from the skin; however, some of the DNA associated peptides may still remain bound to the skin after this treatment. Optionally, the DNA associated peptide-skin complexes are transferred to a new container before contacting with the eluting agent. The eluting agent may be any known eluting agent including, but not limited to, acid (pH 1.5-3.0); base (pH 10-12.5); high salt concentrations such as $MgCl_2$ (3-5 M) and LiCl (5-10 M); water; ethylene glycol (25-50%); dioxane (5-20%); thiocyanate (1-5 M) guanidine (2-5 M); and urea (2-8 M), wherein treatment with an acid is more typical. If the elution buffer used is an acid or base, then, a neutralization buffer is added after the elution step to adjust the pH to the neutral range. Any suitable buffer may be used, wherein 1 M Tris-HCl pH 9.2 is an example of a buffer that may be used with an acid elution buffer.

The eluted DNA associated peptides or the remaining bound DNA associated peptides, or both the eluted DNA associated peptides and the remaining bound DNA associated peptides are then amplified using methods known in the art. For example, the eluted DNA associated peptides and the remaining bound DNA associated peptides may be amplified by infecting/transfecting a bacterial host cell, such as *E. coli* ER2738, as described by Huang et al. (U.S. Patent Application Publication No. 2005/0050656). The infected host cells are grown in a suitable growth medium, such as LB (Luria-Bertani) medium, and this culture is spread onto agar, containing a suitable growth medium, such as LB medium with IPTG (isopropyl β-D-thiogalactopyranoside) and S-Gal™ (3,4-cyclohexenoesculetin-β-D-galactopyranoside). After growth, the plaques are picked for DNA isolation and sequencing to identify the skin-binding peptide sequences.

Alternatively, the eluted DNA associated peptides and the remaining bound DNA associated peptides may be amplified using a nucleic acid amplification method, such as the polymerase chain reaction (PCR), to amplify the DNA comprising the peptide coding region. In that approach, PCR is carried out on the DNA encoding the eluted DNA associated peptides and/or the remaining bound DNA associated peptides using the appropriate primers, as described by Janssen et al. in U.S. Patent Application Publication No. 2003/0152976, which is incorporated herein by reference.

In one embodiment, the eluted DNA associated peptides and the remaining bound DNA associated peptides are amplified by infecting a bacterial host cell as described above, the amplified DNA associated peptides are contacted with a fresh skin sample, and the entire process described above is repeated one or more times to obtain a population that is enriched in skin-binding DNA associated peptides. After the desired number of biopanning cycles, the amplified DNA associated peptide sequences are determined using standard DNA sequencing techniques that are well known in the art to identify the skin-binding peptide sequences. Skin-binding peptide sequences identified using this method include, but are not limited to, SEQ ID NO:1 (Table A).

Additionally, skin care composition resistant skin-binding peptides may be identified using the method described by Wang et al. (copending and commonly owned U.S. patent application Ser. No. 11/359162). In that method, either the initial library of phage peptides is dissolved in a skin care composition matrix for contacting with the skin substrate, or the phage-peptide-skin substrate complex, after it is formed by contacting the substrate with the library of phage peptides, as described above, is contacted with a skin care composition matrix. The biopanning method is then conducted as described above. The skin care composition matrix may be a full strength commercial product or a dilution thereof. Examples of suitable body wash resistant skin-binding peptides are given as SEQ ID NO:22-33 (Table A).

Skin-binding peptide sequences may also be determined using the method described by Lowe in copending and commonly owned U.S. patent application Ser. No. 11/157661. That method provides a means for determining the sequence of a peptide binding motif having affinity for a particular substrate, for example skin. First, a population of binding peptides for the substrate of interest is identified by biopanning using a combinatorial method, such as phage display. Rather than using many rounds of biopanning to identify specific binding peptide sequences and then using standard pattern recognition techniques to identify binding motifs, as is conventionally done in the art, the method requires only a few rounds of biopanning. The sequences in the population of binding peptides, which are generated by biopanning, are analyzed by identifying subsequences of 2, 3, 4, and 5 amino acid residues that occur more frequently than expected by random chance. The identified subsequences are then matched head to tail to give peptide motifs with substrate binding properties. This procedure may be repeated many times to generate long peptide sequences.

Alternatively, skin-binding peptide sequences may be generated empirically by designing peptides that comprise positively charged amino acids, which can bind to skin via electrostatic interaction, as described by Rothe et al. (WO 2004/000257). The empirically generated skin-binding peptides have between about 7 amino acids to about 50 amino acids, and comprise at least about 40 mole % positively charged amino acids, such as lysine, arginine, and histidine. Peptide sequences containing tripeptide motifs such as HRK, RHK, HKR, RKH, KRH, KHR, HKX, KRX, RKX, HRX, KHX and RHX are most preferred where X can be any natural amino acid but is most preferably selected from neutral side chain amino acids such as glycine, alanine, proline, leucine, isoleucine, valine and phenylalanine. In addition, it should be understood that the peptide sequences must meet other functional requirements in the end use including solubility, viscosity and compatibility with other components in a formulated product and will therefore vary according to the needs of the application. In some cases the peptide may contain up to 60 mole % of amino acids not comprising histidine, lysine or arginine. Suitable empirically generated skin-binding peptides include, but are not limited to, SEQ ID NOs:2, 3, 4, 5, and 6 (Table A).

The skin-binding peptide may further comprise at least one cysteine or lysine residue on at least one of the C-terminal end or the N-terminal end of the skin-binding peptide sequence to facilitate coupling with the organic sunscreen agent, as described below. An example of a skin-binding peptide having a lysine residue on the C-terminal end of the binding sequence is given as SEQ ID NO:17.

TABLE A

Examples of Skin-Binding Peptide Sequences

| Peptide | Sequence | SEQ ID NO: |
|---|---|---|
| Skin | TPFHSPENAPGS | 1 |
| Skin (empirical) | KRGRHKRPKRHK | 2 |
| Skin (empirical) | RLLRLLR | 3 |
| Skin (empirical) | HKPRGGRKKALH | 4 |
| Skin (empirical) | KPRPPHGKKHRPKHRPKK | 5 |
| Skin (empirical) | RGRPKKGHGKRPGHRARK | 6 |
| Skin | KQATFPPNPTAY | 7 |
| Skin | HGHMVSTSQLSI | 8 |
| Skin | LSPSRMK | 9 |
| Skin | LPIPRMK | 10 |
| Skin | HQRPYLT | 11 |
| Skin | FPPLLRL | 12 |
| Skin, lysine at C-terminus | TPFHSPENAPGSK | 17 |
| Skin | TPFHSPENAPGSGGGS | 18 |
| Skin | TPFHSPENAPGSGGGSS | 19 |
| Skin | TPFHSPENAPGSGGG | 20 |
| Skin | TPFHSPENAPGS | 21 |
| Skin (Body Wash Resistant) | SVSVGMKPSPRP | 22 |
| Skin (Body Wash Resistant) | TMGFTAPRFPHY | 23 |
| Skin (Body Wash Resistant) | NLQHSVGTSPVW | 24 |
| Skin (Body Wash Resistant) | QLSYHAYPQANHHAP | 25 |
| Skin (Body Wash Resistant) | SGCHLVYDNGFCDH | 26 |
| Skin (Body Wash Resistant) | ASCPSASHADPCAH | 27 |
| Skin (Body Wash Resistant) | NLCDSARDSPRCKV | 28 |
| Skin (Body Wash Resistant) | NHSNWKTAADFL | 29 |
| Skin (Body Wash Resistant) | SDTISRLHVSMT | 30 |
| Skin (Body Wash Resistant) | SPYPSWSTPAGR | 31 |
| Skin (Body Wash Resistant) | DACSGNGHPNNCDR | 32 |
| Skin (Body Wash Resistant) | DWCDTIIPGRTCHG | 33 |

Production of Skin-Binding Peptides

The skin-binding peptides of the present invention may be prepared using standard peptide synthesis methods, which are well known in the art (see for example Stewart et al., *Solid Phase Peptide Synthesis*, Pierce Chemical Co., Rockford, Ill., 1984; Bodanszky, *Principles of Peptide Synthesis*, Springer- Verlag, New York, 1984; and Pennington et al., *Peptide Synthesis Protocols*, Humana Press, Totowa, N.J., 1994). Additionally, many companies offer custom peptide synthesis services.

Alternatively, the peptides of the present invention may be prepared using recombinant DNA and molecular cloning techniques. Genes encoding the skin-binding peptides may be produced in heterologous host cells, particularly in the cells of microbial hosts, as described by Huang et al. (U.S. Patent Application Publication No. 2005/0050656). The peptides when prepared by recombinant DNA and molecular cloning techniques may further comprise a proline (P) residue at the N-terminus and optionally an aspartic acid (D) residue at the C-terminus. These additional residues result from the use of DP cleavage sites to separate the desired peptide sequence from peptide tags, used to promote inclusion body formation, and between tandem repeats of the peptide sequences Peptide-Based Organic Sunscreens The peptide-based organic sunscreens of the present invention are formed by coupling a skin-binding peptide (SBP) with an organic sunscreen agent (OSCA). The skin-binding peptide part of the organic sunscreen binds strongly to the skin, thus keeping the organic sunscreen agent attached to the skin for long lasting protection. Suitable skin-binding peptides include, but are not limited to, the skin binding peptides described above (Table A), specifically, SEQ ID NOs:1-6, and 17-33. Additionally, any known skin-binding peptide sequence may be used, including but not limited to, SEQ ID NO.7, and SEQ ID NOs:8, 9,10, 11, and 12, described by Janssen et al. in U.S. Patent Application Publication No. 2003/0152976 and by Janssen et al. in WO 04048399, respectively. It may also be desirable to link two or more skin-binding peptides together, either directly or through a spacer, to enhance the interaction with the skin. Methods to prepare these multiple skin-binding peptides and suitable spacers are described below.

Organic sunscreen agents are organic chemicals that absorb or scatter ultraviolet light of wavelengths between 290 and 400 nm. Organic sunscreen agents are well known in the art (see for example, Woodin et al., U.S. Pat. No. 5,219,558, which is incorporated herein by reference, in particular column 3 line 35 to column 4 line 23). Suitable examples of organic sunscreen agents include, but are not limited to, para-aminobenzoic acid (PABA), ethyl para-aminobenzoate, amyl para-aminobenzoate, octyl para-aminobenzoate, ethylhexyl dimethyl para-aminobenzoate (Padimate O), ethylene glycol salicylate, phenyl salicylate, octyl salicylate, benzyl salicylate, butylphenyl salicylate, homomenthyl salicylate (Homosalate), ethylhexyl salicylate (Octisalate), triethanolamine salicylate (Trolamine salicylate), benzyl cinnamate, 2-ethoxyethyl para-methoxycinnamate (such as Parsol® available from Givaudan-Roure Co.), ethylhexyl methoxycinnamate (Octinoxate), octyl para-methoxycinnamate, glyceryl mono(2-ethylhexanoate) dipara-methoxycinnamate, isopropyl para-methoxycinnamate, urocanic acid, ethyl urocanate, hydroxymethoxybenzophenone (Benzophenone-3), hydroxymethoxybenzophenonesulfonic acid (Benzophenone-4) and salts thereof, dihydroxymethoxybenzophenone (Benzophenone-8), sodium dihydroxymethoxybenzophenonedisulfonate, dihydroxybenzophenone, tetrahydroxybenzophenone, 4-tert-butyl-4'-methoxydibenzoylmethane (Avobenzone), phenylbenzimidazole sulfonic acid (Ensulizole), 2,4,6-trianilino-p-(carbo-2'-ethylhexyl-1'-oxy)-1,3,5-triazine, octocrylene, menthyl anthranilate (Meradimate), avobenzone, cinnamic acid, and 2-(2-hydroxy-5-methylphenyl)benzotriazole. The sunscreen agent may also be an organic polymer that scatters ultraviolet radiation, thereby enhancing the absorption of the radiation by other sunscreen agents. An example of this type of sunscreen agent is SunSpheres™ Polymer, available from Rohm and Haas Co. (Philadelphia, Pa.).

The peptide-based organic sunscreens of the present invention are prepared by coupling a specific skin-binding peptide to an organic sunscreen agent, either directly or via an optional spacer. The coupling interaction may be a covalent bond or a non-covalent interaction, such as hydrogen bonding, electrostatic interaction, hydrophobic interaction, or Van der Waals interaction. In the case of a non-covalent interaction, the peptide-based organic sunscreen may be prepared by mixing the peptide with the organic sunscreen agent and the optional spacer (if used) and allowing sufficient time for the interaction to occur. The unbound materials may be separated from the resulting peptide-based organic sunscreen using methods known in the art, for example, chromatographic methods.

The peptide-based organic sunscreens of the invention may also be prepared by covalently attaching a specific skin-binding peptide to an organic sunscreen agent, either directly or through a spacer. Any known peptide or protein conjugation chemistry may be used to form the peptide-based organic sunscreens of the present invention. Conjugation chemistries are well-known in the art (see for example, Hermanson, *Bioconjugate Techniques*, Academic Press, New York (1996)). Suitable coupling agents include, but are not limited to, carbodiimide coupling agents, acid chlorides, isocyanates, epoxides, maleimides, and other functional coupling reagents that are reactive toward terminal amine and/or carboxylic acid groups, and sulfhydryl groups on the peptides. Additionally, it may be necessary to protect reactive amine or carboxylic acid groups on the peptide to produce the desired structure for the peptide-based organic sunscreen. The use of protecting groups for amino acids, such as t-butyloxycarbonyl (t-Boc), are well known in the art (see for example Stewart et al., supra; Bodanszky, supra; and Pennington et al., supra). In some cases it may be necessary to introduce reactive groups, such as carboxylic acid, alcohol, amine, isocyanate, or aldehyde groups on the organic sunscreen agent for coupling to the skin-binding peptide. These modifications may be done using routine chemistry such as oxidation, reduction, phosgenation, and the like, which is well known in the art.

It may also be desirable to couple the skin-binding peptide to the organic sunscreen agent via a spacer. The spacer serves to separate the organic sunscreen agent from the peptide to ensure that the agent does not interfere with the binding of the peptide to the skin. The spacer may be any of a variety of molecules, such as alkyl chains, phenyl compounds, ethylene glycol, amides, esters and the like. The spacer may be covalently attached to the peptide and the organic sunscreen agent using any of the coupling chemistries described above. In order to facilitate incorporation of the spacer, a bifunctional coupling agent that contains a spacer and reactive groups at both ends for coupling to the peptide and the organic sunscreen agent may be used.

Additionally, the spacer may be a peptide comprising any amino acid and mixtures thereof. The preferred peptide spacers are comprised of the amino acids proline, lysine, glycine, alanine, and serine, and mixtures thereof. In addition, the peptide spacer may comprise a specific enzyme cleavage site, such as the protease Caspase 3 site, given as SEQ ID NO:13, which allows for the enzymatic removal of the organic sunscreen agent from the skin. The peptide spacer may be from 1 to about 50 amino acids, preferably from 1 to about 20 amino acids in length. Exemplary peptide spacers comprise amino acid sequences including, but are not limited to, SEQ ID NOs:14, 15, and 16. These peptide spacers may be linked to the binding peptide sequence by any method known in the art. For example, the entire binding peptide-peptide spacer diblock may be prepared using the standard peptide synthesis methods described above. In addition, the binding peptide and peptide spacer blocks may be combined using carbodiimide coupling agents (see for example, Hermanson, *Bioconjugate Techniques*, Academic Press, New York (1996)), diacid chlorides, diisocyanates and other difunctional coupling reagents that are reactive to terminal amine and/or carboxylic acid groups on the peptides. Alternatively, the entire skin binding peptide-peptide spacer diblock may be prepared using the recombinant DNA and molecular cloning techniques described above. The spacer may also be a combination of a peptide spacer and an organic spacer molecule, which may be prepared using the methods described above.

It may also be desirable to have multiple skin-binding peptides coupled to the organic sunscreen agent to enhance the interaction between the peptide-based organic sunscreen and the skin. Either multiple copies of the same skin-binding peptide or a combination of different skin-binding peptides may be used. Typically, 1 to about 100 skin-binding peptides can be coupled to an organic sunscreen agent. Additionally, multiple peptide sequences may be linked together and attached to the organic sunscreen agent, as described above. Typically, up to about 100 skin-binding peptides may be linked together. Moreover, multiple organic sunscreen agents (OSCA) may be coupled to the skin-binding peptide. Therefore, in one embodiment of the present invention, the peptide-based sunscreens are compositions consisting of a skin-binding peptide (SBP) and an organic sunscreen agent (OSCA), having the general structure $(SBP_m)_n$-$(OSCA)_y$, where m, n and y independently range from 1 to about 100, preferably from 1 to about 10.

In another embodiment, the peptide-based organic sunscreens contain a spacer (S) separating the skin-binding peptide from the organic sunscreen agent, as described above. Multiple copies of the skin-binding peptide may be coupled to a single spacer molecule. Additionally, multiple copies of the peptides may be linked together via spacers and coupled to the organic sunscreen agent via a spacer. Moreover, multiple organic sunscreen agents (OSCA) may be coupled to the spacer. In this embodiment, the peptide-based organic sunscreens are compositions consisting of a skin-binding peptide, a spacer, and an organic sunscreen agent, having the general structure $[(SBP)_x$-$S_m]_n$-$(OSCA)_y$, where x ranges from 1 to about 10, preferably x is 1, and m, n and y independently range from 1 to about 100, preferably from 1 to about 10.

It should be understood that as used herein, SBP is a generic designation and is not meant to refer to a single skin-binding peptide sequence. Where m, n or x as used above, is greater than 1, it is well within the scope of the invention to provide for the situation where a series of skin-binding peptides of different sequences may form a part of the composition. In addition, "S" is also a generic term and is not meant to refer to a single spacer. Where m or n, as used above, is greater than 1, it is well within the scope of the invention to provide for the situation where a number of different spacers may form part of the composition. Additionally, it should be understood that these structures do not necessarily represent a covalent bond between the peptide, the organic sunscreen agent, and the optional spacer. As described above, the coupling interaction between the peptide, the organic sunscreen agent, and the optional spacer may be either covalent or non-covalent.

Sunscreen Compositions

The peptide-based organic sunscreens of the invention may be used in sunscreen products and as an additive in skin care and cosmetic products, such as skin conditioners, moisturizers, foundations, anti-wrinkle products, skin cleansers, body washes, and lipsticks, to protect the skin from damage caused by ultraviolet radiation from the sun. The term "sunscreen composition", as used herein, refers to any skin care or cosmetic composition that comprises at least one peptide-based organic sunscreen of the invention. The sunscreen compositions of the present invention include any composition that may be topically applied to the skin or lips, including but not limited to, lotions, creams, gels, sticks, sprays, ointments, cleansing liquid washes, cleansing solid bars, pastes, foams, powders, shaving creams, lip balms, lipsticks, and wipes.

The sunscreen compositions of the invention may comprise several types of cosmetically-acceptable topical carriers including, but not limited to, solutions, colloidal suspensions, dispersions, emulsions (microemulsions, nanoemulsions, multiple and non-aqeous emulsions), hydrogels, and vesicles (liposomes, niosomes, novasomes). Components and formulation methods of suitable cosmetically-acceptable topical carriers are well known in the art and are described for example by Sieberg et al. (U.S. Pat. No. 6,797,697), Kumar (U.S. Patent Application Publication No. 2005/0142094), and Schultz et al. (U.S. Patent Application Publication No. 2005/0008604), all of which are incorporated herein by reference. Those skilled in the art will appreciate the various methods for producing these various product forms.

The sunscreen compositions of the invention comprise an effective amount of a peptide-based organic sunscreen or a mixture of different peptide-based organic sunscreens in a cosmetically acceptable medium. An effective amount of a peptide-based organic sunscreen for use in a sunscreen composition is herein defined as a proportion of from about 0.01% to about 30%, preferably from about 0.01% to about 10% by weight relative to the total weight of the composition, the amount depending on the desired sun protection factor (SPF) of the formulation. The sunscreen composition may further comprise other sunscreen agents for additional sunscreen capability. These additional sunscreen agents may be organic sunscreen agents including organic polymers that scatter ultraviolet radiation, as described above; inorganic sunscreen agents, such as titanium dioxide, zinc oxide, cerium oxide, or iron oxide; peptide-based inorganic sunscreen agents, as described by Buseman-Williams et al. (copending and commonly owned U.S. Patent Application Publication No. 2005/0249682, which is incorporated herein by reference); and mixtures thereof.

Typically, the cosmetically acceptable medium for sunscreen compositions comprises water and other solvents which include, but are not limited to, mineral oils and fatty alcohols. The cosmetically-acceptable medium is from about 10% to about 99.99% by weight of the composition, preferably from about 50% to about 99% by weight of the composition, and can, in the absence of other additives, form the balance of the composition.

The sunscreen composition may further comprise the following basic cosmetic raw materials, including, but not limited to, hydrocarbons, esters, fatty alcohols, fatty acids, emulsifying agents, humectants, viscosity modifiers, and silicone based materials. The compositions of the present invention may contain a wide range of these basic components. The total concentration of added ingredients usually is less than 50%, preferably less than 20%, and most preferably less than 10% by weight of the total composition. Those skilled in the art will appreciate the various concentrations and combinations for employing these basic components to achieve the desired product form.

Suitable hydrocarbons which may be used in the compositions of the invention include, but are not limited to, mineral oil, isohexadecane, squalane, hydrogenated polyisobutene, petrolatum, paraffin, microcrystalline wax, and polyethylene.

Suitable esters which may be used in the compositions of the invention include, but are not limited to, isopropyl palmitate, octyl stearate, caprylic/capric triglyceride, plant waxes (Canelilla, Caranauba), vegetable oils (natural glycerides) and plant oils (Jojoba).

Suitable fatty alcohols which may be used in the compositions of the invention include, but are not limited to, myristyl, cety, oleyl, stearyl, isostearyl, and behenyl.

Suitable emulsifying agents which may be used in the compositions of the invention include, but are not limited to, anionic (TEA/K stearate (triethanolamine/potassium stearate), sodium lauryl stearate, sodium cetearyl sulfate, and beeswax/Borax), nonionic (glycerol di-stearate, PEG (polyethyleneglycol)-100 Stearate, Polysorbate 20, steareth 2 and steareth 20), and cationic (distearyidimethylammonium chloride, behenalkonium chloride and steapyrium chloride), polymeric (acrylates/C10-30 alkyl acrylate crosspolymer, polyacrylamide, polyquaternium-37, propylene glycol, dicaprylate/dicaparate and PPG-1 Trideceth-6), and silicone-based materials (alkyl modified dimethicone copolyols), and polyglyceryl esters, and ethoxylated di-fatty esters.

Exemplary humectants for use in the compositions of the invention include, but are not limited to, propylene glycol, sorbitol, butylene glycol, hexylene glycol, acetamide MEA (acetylethanolamine), honey, and sodium PCA (sodium-2-pyrrolidone carboxylate).

Viscosity modifiers which may be used in the compositions of the invention include, but are not limited to, xanthum gum, magnesium aluminum silicate, cellulose gum and hydrogenated castor oil.

Further, the sunscreen compositions may comprise one or more conventional functional cosmetic or dermatological additives or adjuvants, providing that they do not interfere with the mildness, performance or aesthetic characteristics desired in the final products. The CTFA Cosmetic Ingredient Handbook, Eight Edition (2000), and McCutheon's Functional Materials, North America and Internationals Editions, MC Publishing Co. (2003), which are incorporated herein by reference in their entirety, describe a wide variety of cosmetic and pharmaceutical ingredients commonly used in skin care and cosmetic compositions, which are suitable for use in the compositions of the present invention. The compositions of the present invention may contain a wide range of these additional, optional components. The total concentration of added ingredients usually is less than about 20%, preferably less than about 5%, and most preferably less than about 3% by weight of the total composition. Such components include, but are not limited to, surfactants, emollients, moisturizers, stabilizers, film-forming substances, fragrances, colorants, chelating agents, preservatives, antioxidants, pH adjusting agents, antimicrobial agents, water-proofing agents, dry feel modifiers, vitamins, plant extracts, hydroxy acids, and sunless tanning agents. Examples of common raw materials and suitable adjuvants for a sunscreen composition are described by Fowler et al U.S. Pat. No. 6,858,200, and Nicoll et al., U.S. Pat. No. 5,188,831, both of which are incorporated herein by reference.

Methods for Treating Skin and Lips

In another embodiment, a method is provided for treating skin or lips with the sunscreen compositions of the invention. Specifically, the present invention also comprises a method for forming a protective film of peptide-based organic sunscreen on the skin or lips by applying one of the compositions described above comprising an effective amount of a peptide-based organic sunscreen to the skin or lips and allowing the formation of the protective film. The compositions of the present invention may be applied to the skin or lips by various means, including, but not limited to spraying, brushing, and applying by hand.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "g" means gram(s), "mg" means milligram(s), "mol" means mole(s), "mL" means milliliter(s), "h" means hour(s), "wt %" means percent by weight, "qs" means as much as suffices, "MALDI mass spectrometry" means matrix-assisted, laser desorption ionization mass spectrometry.

Example 1 (Prophetic)

Preparation of a Peptide-Based Organic Sunscreen

The purpose of this prophetic example is to describe how to prepare a peptide-based organic sunscreen by covalently coupling an active ultraviolet radiation absorbing sunscreen agent, specifically, avobenzone analog moiety, to a skin-binding peptide.

1,3-Propanedione,1-[4-(1,1-dimethylethyl)phenyl]-3-(4-hydroxyphenyl)-(9Cl) (CAS No. 132944-34-4), which is obtained from Vivimed Labs, Ltd. (Surrey, United Kingdom), is dissolved in toluene and heated with excess glutaraldehyde to completely cap the hydroxy groups with aldehyde groups. The excess glutaraldehyde is removed by distillation at reduced pressure and the aldehyde-capped adduct is dissolved in dimethylformamide (DMF). A skin-binding peptide having an added lysine residue at the C-terminal end, given as SEQ ID NO:17, is then added and is covalently coupled via pendant free aldehyde units on the capped adduct and an amine group on the peptide. The product is isolated by distillation of the solvent at reduced pressure and the product is stored under vacuum until free of detectable DMF. The formation of the peptide-based sunscreen is confirmed using MALDI mass spectrometry.

Example 2 (Prophetic)

Preparation of a Peptide-Based Organic Sunscreen

The purpose of this prophetic example is to describe how to prepare a peptide-based organic sunscreen by covalently coupling an active ultraviolet radiation absorbing para aminobenzoic acid analog moiety with a skin-binding peptide.

4-Aminobenzoic acid (CAS No. 99-05-8, Aldrich, Milwaukee, Wis.) is dissolved in DMF and heated with excess glutaraldehyde to completely cap the amine groups with aldehyde groups. The excess glutaraldehyde is removed by distillation at reduced pressure. A skin-binding peptide having a lysine residue at the C-terminal end, given as SEQ ID NO:17, is then added and allowed to react for 72 h. The peptide is covalently coupled via pendant free aldehyde groups on the capped adduct and an amine group on the peptide. The product is isolated by distillation of the solvent at reduced pressure and the product is stored under vacuum until free of detectable DMF. The formation of the peptide-based sunscreen is confirmed using MALDI mass spectrometry.

Example 3

Preparation of a Peptide-Based Organic Sunscreen

The purpose of this Example was to prepare a peptide-based organic sunscreen by covalently coupling acyl chloride functionalized cinnamic acid to a skin-binding peptide.

Acyl chloride functionalized cinnamic acid (16.5 mg, CAS No. 102-92-1, obtained from Aldrich) was dissolved in 3 mL of 1-methyl-2-pyrrolidone (NMP) and added to a solution containing 50 mg of non-protected skin-binding peptide (70% specific peptide mixture obtained from Synpep Inc., Dublin, Calif.; the major peptide component is given as SEQ ID NO:18; the remaining peptide components are given as SEQ ID NOs:19-21) dissolved in 15 mL of NMP containing triethylamine (3 mg). The resulting solution was stirred at room temperature for 72 h. After this time, the solvent was evaporated, yielding a yellowish-brown viscous wax residue. The product was analyzed by gas chromatography—MALDI mass spectrometry and found to contain components having molecular weights of 1283 g/mol, 1542 g/mol, 1629 g/mol, and 1716 g/mol, consistent with covalent attachment of 1 mol of acyl chloride to the peptides in the mixture and molecular weights of 1760 g/mol and 1847 g/mol, consistent with covalent attachment of 2 moles of acyl chloride to the peptides. These results are consistent with the peptide molecular weight distribution in starting peptide mixture.

Example 4 (Prophetic)

Water-Resistant Sunscreen Lotion

The purpose of this prophetic Example is to describe the preparation of a water-resistant sunscreen lotion comprising a peptide-based organic sunscreen.

The water-resistant, water in oil (W/O) sunscreen lotion is prepared by combining the ingredients given in Table 1 using conventional mixing techniques.

TABLE 1

Water-Resistant Sunscreen Lotion Ingredients

| Ingredient | Wt % |
|---|---|
| Cyclomethicone & dimethicone copolyol | 5.0 |
| Dimethicone | 10.0 |
| Peptide-based organic sunscreen, as described in Example 1, or 3 | 12.0 |
| Sodium chloride | 1.0 |
| Quaternium 15 | 0.1 |
| Water | qs to 100% |

Example 5 (Prophetic)

High SPF Water-Resistant Sunscreen Cream

The purpose of this prophetic Example is to describe the preparation of a high SPF water-resistant sunscreen cream comprising a peptide-based organic sunscreen.

The high SPF water-resistant sunscreen cream is prepared by combining the ingredients given in Table 2 using conventional mixing techniques.

TABLE 2

High SPF Water Resistant Sunscreen Cream Ingredients

| Ingredient | Wt % |
|---|---|
| Cetyl dimethicone copoloyl | 5.0 |
| Cetyl dimethicone | 2.5 |
| Cyclomethicone | 7.5 |
| Ceresin wax | 1.0 |
| Peptide-based metal oxide sunscreen agent* | 15.0 |
| Peptide-based organic sunscreen, as described in Example 1, 2, or 3 | 15.0 |
| Hydrogenated castor oil | 0.5 |
| Magnesium sulfate | 0.75 |
| Germaben II ® (Propylene gylcol, diazolidinyl urea, methylparaben and propylparaben preservative mixture); Sutton Labs, Chatham, NJ) | 1.0 |
| Water | qs to 100% |

*Prepared as described by Buseman-Williams et al. (copending and commonly owned U.S. Patent Application Publication No. 2005/0249682, Example 12).

Example 6 (Prophetic)

Spray-On Sunscreen Composition

The purpose of this prophetic Example is to describe the preparation of a spray-on sunscreen composition comprising peptide-based organic sunscreens.

The spray-on sunscreen is prepared by combining the ingredients given in Table 3 using conventional mixing techniques.

TABLE 3

Spray-On Sunscreen Ingredients

| Ingredient | Wt % |
|---|---|
| Propylene glycol | 2.5 |
| Xanthum gum | 0.05 |
| Peptide-based organic sunscreen, as described in Example 1 | 7.5 |
| Peptide-based organic sunscreen, as described in Example 2 | 3.5 |
| PEG-40 Stearate | 0.1 |
| Octyl palmitate | 7.5 |
| Acrylates/$C_{10-30}$ alkyl acrylates cross polymer | 0.2 |
| Triethanolamine | 0.18 |
| Methylparaben | 0.5 |
| Phenoxyethanol | 0.5 |
| Water | qs to 100% |

What is claimed is:

1. A peptide-based organic sunscreen having the general structure $(SBP_m)_n$—$(OSCA)_y$, wherein
   a) SBP is a skin-binding peptide comprising between about 7 to about 50 amino acids and further comprising an amino acid sequence selected from the group consisting of SEQ ID NO: 1, 2, 3, 4, 5, 6, 7, 8, 9, 10,11, 12, 17, 18, 19, 20, 21, 22, 23, 24, 25, 26, 27, 28, 29, 30, 31, 32, and 33;

b) OSCA is an organic sunscreen agent;

c) m ranges from 1 to about 100;

d) n ranges from 1 to about 100; and e) y ranges from 1 to about 100, wherein the organic sunscreen agent is selected from the group consisting of of: para-aminobenzoic acid, ethyl para-aminobenzoate, amyl para-aminobenzoate, octyl para-aminobenzoate, ethylhexyl dimethyl para-aminobenzoate, ethylene glycol salicylate, phenyl salicylate, octyl salicylate, benzyl salicylate, butylphenyl salicylate, homomenthyl salicylate, triethanolamine salicylate, benzyl cinnamate, 2-ethoxyethyl para-methoxycinnamate, ethylhexyl methoxycinnamate, glyceryl mono(2-ethylhexanoate) dipara-methoxycinnamate, isopropyl para-methoxycinnamate, urocanic acid, ethyl urocanate, hydroxymethoxybenzophenone, dihydroxymethoxybenzophenone, sodium dihydroxymethoxybenzophenonedisulfonate, dihydroxybenzophenone, tetrahydroxybenzophenone, 4-tert-butyl-4'-methoxydibenzoylmethane, 2,4,6-trianilino-p-(carbo-2'-ethylhexyl-1'-oxy)-1,3,5-triazine, octocrylene, menthyl anthranilate, 2-(2-hydroxy-5-methylphenyl)benzotriazole, avobenzone, cinnamic acid, and organic polymers that scatter ultraviolet radiation.

2. A peptide-based organic sunscreen having the general structure $[(SBP)_x$—$S_m]_n$—$(OSCA)_y$, wherein a) SBP is a skin-binding peptide comprising between about 7 to about 50 amino acids and further comprising an amino acid sequence selected from the group consisting of SEQ ID NO: 1, 2, 3, 4, 5, 6, 7, 8, 9, 10, 11, 12, 17, 18, 19, 20, 21, 22, 23, 24, 25, 26, 27, 28, 29, 30, 31, 32, and 33;

b) OSCA is an organic sunscreen agent;

c) S is a spacer;

d) x ranges from 1 to about 10;

e) m ranges from 1 to about 100;

f) n ranges from 1 to about 100; and g) y ranges from 1 to about 100;

wherein the organic sunscreen agent is selected from the group consisting of of: para-aminobenzoic acid, ethyl para-aminobenzoate, amyl para-aminobenzoate, octyl para-aminobenzoate, ethylhexyl dimethyl para-aminobenzoate, ethylene glycol salicylate, phenyl salicylate, octyl salicylate, benzyl salicylate, butylphenyl salicylate, homomenthyl salicylate, triethanolamine salicylate, benzyl cinnamate, 2-ethoxyethyl para-methoxycinnamate, ethylhexyl methoxycinnamate, glyceryl mono(2-ethylhexanoate) dipara-methoxycinnamate, isopropyl para-methoxycinnamate, urocanic acid, ethyl urocanate, hydroxymethoxybenzophenone, dihydroxymethoxybenzophenone, sodium dihydroxymethoxybenzophenonedisulfonate, dihydroxybenzophenone, tetrahydroxybenzophenone, 4-tert-butyl-4'-methoxydibenzoylmethane, 2,4,6-trianilino-p-(carbo-2'-ethylhexyl-1'-oxy)-1,3,5-triazine, octocrylene, menthyl anthranilate, 2-(2-hydroxy-5-methylphenyl)benzotriazole, avobenzone, cinnamic acid, and organic polymers that scatter ultraviolet radiation.

3. A peptide-based organic sunscreen according to either of claims 1 or 2 wherein the skin-binding peptide is from about 7 to about 25 amino acids in length.

4. A peptide-based organic sunscreen according to either of claims 1 or 2 wherein the skin-binding peptide is from about 7 to about 20 amino acids in length.

5. A peptide-based organic sunscreen according to either of claims 1 or 2 wherein the skin-binding peptide is generated combinatorially by a process selected from the group consisting of phage display, yeast display, and bacterial display.

6. A peptide-based organic sunscreen according to either of claims 1 or 2 wherein the skin-binding peptide is generated empirically.

7. A peptide-based organic sunscreen according to either of claims 1 or 2 wherein the skin-binding peptide further comprises a cysteine residue on at least one end of the peptide selected from the group consisting of
   a) the N-terminal end; and
   b) the C-terminal end.

8. A peptide-based organic sunscreen according to either of claims 1 or 2 wherein the skin-binding peptide further comprises a lysine residue on at least one end of the peptide selected from the group consisting of
   a) the N-terminal end; and
   b) the C-terminal end.

9. A peptide-based organic sunscreen according to either of claims 1 or 2 wherein the skin-binding peptide is identified by a process comprising the steps of:
   (a) providing a combinatorial library of DNA associated peptides;
   (b) contacting the library of (a) with a skin sample to form a reaction solution comprising DNA associated peptide-skin complexes;
   (c) isolating the DNA associated peptide-skin complexes of (b);
   (d) amplifying the DNA encoding the peptide portion of the DNA associated peptide-skin complexes of (c); and
   (e) sequencing the amplified DNA of (d) encoding a skin-binding peptide, wherein the skin-binding peptide is identified.

10. A peptide-based organic sunscreen according to claim 9 wherein after step (c):
    i) the DNA associated peptide-skin complexes are contacted with an eluting agent whereby a portion of DNA associated peptides are eluted from the skin and a portion of the DNA associated peptides remain complexed; and
    ii) the eluted or complexed DNA associated peptides of (i) are subjected to steps (d) and (e).

11. A peptide-based organic sunscreen according to claim 9 wherein the DNA encoding the peptides is amplified by a process selected from the group consisting of:
    a) amplifying DNA comprising a peptide coding region by polymerase chain reaction; and
    b) infecting a host cell with a phage comprising DNA encoding the peptide and growing said host cell in a suitable growth medium.

12. A peptide-based organic sunscreen according to claim 9 wherein the peptides encoded by the amplified DNA of step (d) are contacted with a fresh skin sample and steps (b) through (d) are repeated one or more times.

13. A peptide-based organic sunscreen according to claim 2 wherein the spacer is a peptide comprising amino acids selected from the group consisting of proline, lysine, glycine, alanine, serine, and mixtures thereof.

14. A peptide-based organic sunscreen according to claim 13 wherein the peptide spacer is from 1 to about 50 amino acids in length.

15. A peptide-based organic sunscreen according to claim 2 wherein the peptide spacer comprises an amino acid sequence selected from the group consisting of SEQ ID NO:13, 14, 15, and 16.

16. A peptide-based organic sunscreen according to claim 2 wherein the spacer is selected from the group consisting of ethanol amine, ethylene glycol, polyethylene with a chain length of 6 carbon atoms, polyethylene glycol with 3 to 6 repeating units, phenoxyethanol, propanolamide, butylene glycol, butyleneglycolamide, propyl phenyl, ethyl alkyl chain, propyl alkyl chain, hexyl alkyl chain, steryl alkyl chains, cetyl alkyl chains, and palmitoyl alkyl chains.

17. A sunscreen composition comprising an effective amount of the peptide-based organic sunscreen according to either of claims 1 or 2.

18. A sunscreen composition according to claim 17 wherein the composition is in a form selected from the group consisting of: a lotion, a cream, a gel, a stick, a spray, an ointment, a cleansing liquid wash, a cleansing solid bar, a paste, a foam, a powder, a shaving cream, a lip balm, a lipstick, and a wipe.

19. A sunscreen composition according to claim 17 wherein the composition further comprises at least one cosmetic raw material or adjuvant selected from the group consisting of: hydrocarbons, esters, fatty alcohols, fatty acids, emulsifying agents, humectants, viscosity modifiers, silicone based materials, surfactants, emollients, moisturizers, stabilizers, film-forming substances, fragrances, colorants, chelating agents, preservatives, antioxidants, pH adjusting agents, antimicrobial agents, water-proofing agents, dry feel modifiers, vitamins, plant extracts, hydroxy acids, organic sunscreen agents, inorganic sunscreen agents, peptide-based inorganic sunscreen agents, and sunless tanning agents.

20. A method for forming a protective layer of a peptide-based organic sunscreen on the skin or lips comprising applying the composition of claim 17 to the skin or lips and allowing the formation of said protective layer.

\* \* \* \* \*

SEQUENCE LISTING

<160> NUMBER OF SEQ ID NOS: 33

<210> SEQ ID NO 1
<211> LENGTH: 12
<212> TYPE: PRT
<213> ORGANISM: Artificial Sequence
<220> FEATURE:
<223> OTHER INFORMATION: Skin-Binding Peptide

<400> SEQUENCE: 1

Thr Pro Phe His Ser Pro Glu Asn Ala Pro Gly Ser
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Skin-Binding Peptide

<400> SEQUENCE: 2

Lys Arg Gly Arg His Lys Arg Pro Lys Arg His Lys
1               5                   10

<210> SEQ ID NO 3
<211> LENGTH: 7
<212> TYPE: PRT
<213> ORGANISM: Artificial Sequence
<220> FEATURE:
<223> OTHER INFORMATION: Skin-Binding Peptide

<400> SEQUENCE: 3

Arg Leu Leu Arg Leu Leu Arg
1               5

<210> SEQ ID NO 4
<211> LENGTH: 12
<212> TYPE: PRT
<213> ORGANISM: Artificial Sequence
<220> FEATURE:
<223> OTHER INFORMATION: Skin-Binding Peptide

<400> SEQUENCE: 4

His Lys Pro Arg Gly Gly Arg Lys Lys Ala Leu His
1               5                   10

<210> SEQ ID NO 5
<211> LENGTH: 18
<212> TYPE: PRT
<213> ORGANISM: Artificial Sequence
<220> FEATURE:
<223> OTHER INFORMATION: Skin-Binding Peptide

<400> SEQUENCE: 5

Lys Pro Arg Pro Pro His Gly Lys Lys His Arg Pro Lys His Arg Pro
1               5                   10                  15

Lys Lys

<210> SEQ ID NO 6
<211> LENGTH: 18
<212> TYPE: PRT
<213> ORGANISM: Artificial Sequence
<220> FEATURE:
<223> OTHER INFORMATION: Skin-Binding Peptide

<400> SEQUENCE: 6

Arg Gly Arg Pro Lys Lys Gly His Gly Lys Arg Pro Gly His Arg Ala
1               5                   10                  15

Arg Lys

<210> SEQ ID NO 7
<211> LENGTH: 12
<212> TYPE: PRT
<213> ORGANISM: Artificial Sequence
<220> FEATURE:
<223> OTHER INFORMATION: Skin-Binding Peptide

<400> SEQUENCE: 7

Lys Gln Ala Thr Phe Pro Pro Asn Pro Thr Ala Tyr
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Skin-Binding Peptide

<400> SEQUENCE: 8

His Gly His Met Val Ser Thr Ser Gln Leu Ser Ile
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Skin-Binding Peptide

<400> SEQUENCE: 9

Leu Ser Pro Ser Arg Met Lys
1               5

<210> SEQ ID NO 10
<211> LENGTH: 7
<212> TYPE: PRT
<213> ORGANISM: Artificial Sequence
<220> FEATURE:
<223> OTHER INFORMATION: Skin-Binding Peptide

<400> SEQUENCE: 10

Leu Pro Ile Pro Arg Met Lys
1               5

<210> SEQ ID NO 11
<211> LENGTH: 7
<212> TYPE: PRT
<213> ORGANISM: Artificial Sequence
<220> FEATURE:
<223> OTHER INFORMATION: Skin-Binding Peptide

<400> SEQUENCE: 11

His Gln Arg Pro Tyr Leu Thr
1               5

<210> SEQ ID NO 12
<211> LENGTH: 7
<212> TYPE: PRT
<213> ORGANISM: Artificial Sequence
<220> FEATURE:
<223> OTHER INFORMATION: Skin-Binding Peptide

<400> SEQUENCE: 12

Phe Pro Pro Leu Leu Arg Leu
1               5

<210> SEQ ID NO 13
<211> LENGTH: 8
<212> TYPE: PRT
<213> ORGANISM: Artificial Sequence
<220> FEATURE:
<223> OTHER INFORMATION: Caspase 3 Cleavage Site

<400> SEQUENCE: 13

Leu Glu Ser Gly Asp Glu Val Asp
1               5

<210> SEQ ID NO 14
<211> LENGTH: 37
<212> TYPE: PRT
<213> ORGANISM: Artificial Sequence
<220> FEATURE:
<223> OTHER INFORMATION: Peptide Spacer

<400> SEQUENCE: 14

Thr Ser Thr Ser Lys Ala Ser Thr Thr Thr Ser Ser Lys Thr Thr
1               5                   10                  15

Thr Thr Ser Ser Lys Thr Thr Thr Thr Thr Ser Lys Thr Ser Thr Thr
            20                  25                  30

Ser Ser Ser Ser Thr
        35

<210> SEQ ID NO 15
<211> LENGTH: 22
<212> TYPE: PRT
<213> ORGANISM: Artificial Sequence
<220> FEATURE:
<223> OTHER INFORMATION: Peptide Spacer 2

<400> SEQUENCE: 15

Gly Gln Gly Gly Tyr Gly Gly Leu Gly Ser Gln Gly Ala Gly Arg Gly
1               5                   10                  15

Gly Leu Gly Gly Gln Gly
            20

<210> SEQ ID NO 16
<211> LENGTH: 10
<212> TYPE: PRT
<213> ORGANISM: Artificial Sequence
<220> FEATURE:
<223> OTHER INFORMATION: Peptide Spacer

<400> SEQUENCE: 16

Gly Pro Gly Gly Tyr Gly Pro Gly Gln Gln
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Skin-Binding Peptide

<400> SEQUENCE: 17

Thr Pro Phe His Ser Pro Glu Asn Ala Pro Gly Ser Lys
1               5                   10

<210> SEQ ID NO 18

```
<211> LENGTH: 16
<212> TYPE: PRT
<213> ORGANISM: Artificial Sequence
<220> FEATURE:
<223> OTHER INFORMATION: Skin-binding peptide

<400> SEQUENCE: 18

Thr Pro Phe His Ser Pro Glu Asn Ala Pro Gly Ser Gly Gly Gly Ser
1               5                   10                  15

<210> SEQ ID NO 19
<211> LENGTH: 17
<212> TYPE: PRT
<213> ORGANISM: Artificial Sequence
<220> FEATURE:
<223> OTHER INFORMATION: Skin-binding peptide

<400> SEQUENCE: 19

Thr Pro Phe His Ser Pro Glu Asn Ala Pro Gly Ser Gly Gly Gly Ser
1               5                   10                  15

Ser

<210> SEQ ID NO 20
<211> LENGTH: 15
<212> TYPE: PRT
<213> ORGANISM: Artificial Sequence
<220> FEATURE:
<223> OTHER INFORMATION: Skin-binding peptide

<400> SEQUENCE: 20

Thr Pro Phe His Ser Pro Glu Asn Ala Pro Gly Ser Gly Gly Gly
1               5                   10                  15

<210> SEQ ID NO 21
<211> LENGTH: 12
<212> TYPE: PRT
<213> ORGANISM: Artificial Sequence
<220> FEATURE:
<223> OTHER INFORMATION: Skin-binding peptide

<400> SEQUENCE: 21

Thr Pro Phe His Ser Pro Glu Asn Ala Pro Gly Ser
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Body wash resistant skin-binding peptide

<400> SEQUENCE: 22

Ser Val Ser Val Gly Met Lys Pro Ser Pro Arg Pro
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Body wash resistant skin-binding peptide

<400> SEQUENCE: 23

Thr Met Gly Phe Thr Ala Pro Arg Phe Pro His Tyr
1               5                   10

<210> SEQ ID NO 24
```

-continued

<211> LENGTH: 12
<212> TYPE: PRT
<213> ORGANISM: Artificial Sequence
<220> FEATURE:
<223> OTHER INFORMATION: Body wash resistant skin-binding peptide

<400> SEQUENCE: 24

Asn Leu Gln His Ser Val Gly Thr Ser Pro Val Trp
1 5 10

<210> SEQ ID NO 25
<211> LENGTH: 15
<212> TYPE: PRT
<213> ORGANISM: Artificial Sequence
<220> FEATURE:
<223> OTHER INFORMATION: Body wash resistant skin-binding peptide

<400> SEQUENCE: 25

Gln Leu Ser Tyr His Ala Tyr Pro Gln Ala Asn His His Ala Pro
1 5 10 15

<210> SEQ ID NO 26
<211> LENGTH: 14
<212> TYPE: PRT
<213> ORGANISM: Artificial Sequence
<220> FEATURE:
<223> OTHER INFORMATION: Body wash resistant skin-binding peptide

<400> SEQUENCE: 26

Ser Gly Cys His Leu Val Tyr Asp Asn Gly Phe Cys Asp His
1 5 10

<210> SEQ ID NO 27
<211> LENGTH: 14
<212> TYPE: PRT
<213> ORGANISM: Artificial Sequence
<220> FEATURE:
<223> OTHER INFORMATION: Body wash resistant skin-binding peptide

<400> SEQUENCE: 27

Ala Ser Cys Pro Ser Ala Ser His Ala Asp Pro Cys Ala His
1 5 10

<210> SEQ ID NO 28
<211> LENGTH: 14
<212> TYPE: PRT
<213> ORGANISM: Artificial Sequence
<220> FEATURE:
<223> OTHER INFORMATION: Body wash resistant skin-binding peptide

<400> SEQUENCE: 28

Asn Leu Cys Asp Ser Ala Arg Asp Ser Pro Arg Cys Lys Val
1 5 10

<210> SEQ ID NO 29
<211> LENGTH: 12
<212> TYPE: PRT
<213> ORGANISM: Artificial Sequence
<220> FEATURE:
<223> OTHER INFORMATION: Body wash resistant skin-binding peptide

<400> SEQUENCE: 29

Asn His Ser Asn Trp Lys Thr Ala Ala Asp Phe Leu
1 5 10

<210> SEQ ID NO 30
<211> LENGTH: 12
<212> TYPE: PRT

```
<213> ORGANISM: Artificial Sequence
<220> FEATURE:
<223> OTHER INFORMATION: Body wash resistant skin-binding peptide

<400> SEQUENCE: 30

Ser Asp Thr Ile Ser Arg Leu His Val Ser Met Thr
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Body wash resistant skin-binding peptide

<400> SEQUENCE: 31

Ser Pro Tyr Pro Ser Trp Ser Thr Pro Ala Gly Arg
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Body wash resistant skin-binding peptide

<400> SEQUENCE: 32

Asp Ala Cys Ser Gly Asn Gly His Pro Asn Asn Cys Asp Arg
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Body wash resistant skin-binding peptide

<400> SEQUENCE: 33

Asp Trp Cys Asp Thr Ile Ile Pro Gly Arg Thr Cys His Gly
1               5                   10
```